United States Patent [19]

Cassinelli et al.

[11] Patent Number: 4,895,933
[45] Date of Patent: Jan. 23, 1990

[54] NEW ANTITUMOR AGENT OBTAINED BY MICROBIAL STEREOSELECTIVE REDUCTION OF 4'-DEOXY-4'-IODODOXORUBICIN

[75] Inventors: Giuseppe Cassinelli, Voghera; Teresa Bordoni, Milan; Sergio Merli, Bernareggio; Giovanni Rivola, Milan, all of Italy

[73] Assignee: Farmitalia Carlo Erba S.p.A., Milan, Italy

[21] Appl. No.: 145,282

[22] Filed: Jan. 19, 1988

[30] Foreign Application Priority Data

Jan. 22, 1987 [GB] United Kingdom ................. 8701381

[51] Int. Cl.$^4$ ............................................. C07H 15/24
[52] U.S. Cl. ..................................... 536/6.4; 435/78; 435/886
[58] Field of Search ........................... 536/6.4; 514/34; 435/78, 886

[56] References Cited

U.S. PATENT DOCUMENTS 4,427,664  1/1984  Horton et al. ...................... 536/6.4

Primary Examiner—Herbert J. Lilling
Assistant Examiner—Elli Peselev
Attorney, Agent, or Firm—Oblon, Spivak, McClelland, Maier & Neustadt

[57] ABSTRACT

4'-Deoxy-13(S)-dihydro-4'-iododoxorubicin having the formula (II):

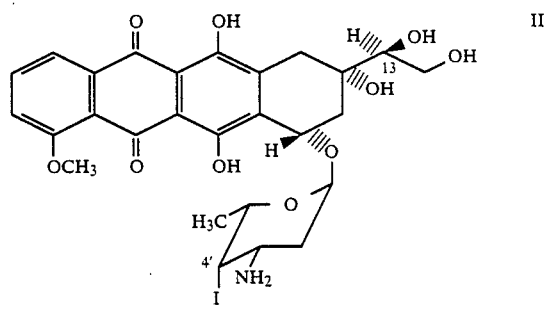

and pharmaceutically acceptable salts thereof are antitumor agents.

2 Claims, No Drawings

NEW ANTITUMOR AGENT OBTAINED BY MICROBIAL STEREOSELECTIVE REDUCTION OF 4'-DEOXY-4'-IODODOXORUBICIN

DESCRIPTION

The present invention relates to a doxorubicin derivative, its preparation and pharmaceutical compositions containing it.

Accordingly, the present provides 4'-deoxy-13(S)-dihydro-4'-iododoxorubicin having the formula (II)

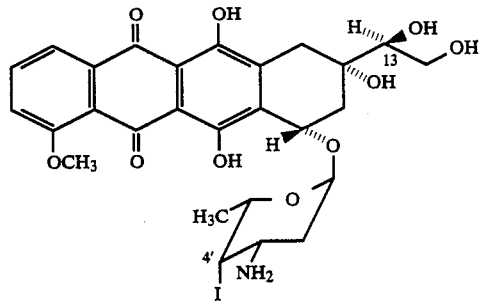

and pharmaceutically acceptable salts thereof.

A microorganism belonging to the genera Streptomyces is employed for a stereoselective reduction of the 13-ketone functional group of 4'-deoxy-4'-iododoxorubicin (I)

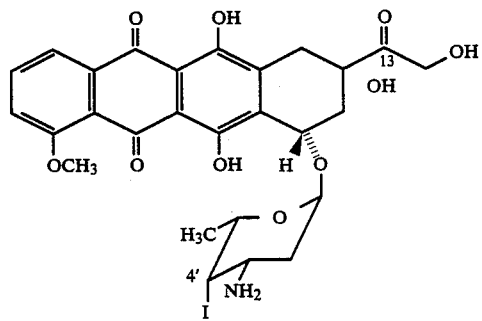

to give specifically 4'-deoxy-13-(S)-dihydro-4'-iododoxorubicin, one of the two possible C-13 stereoisomeric 4'-deoxy-13-dihydro-4'-iododoxorubicins. The new compound (II), hereinafter designated FCE 24883, is useful as an anti-tumor agent and displays on experimental tumors an activity comparable with that of 4'-deoxy-4'-iododoxorubicin (I). The substrate for the microbial stereoselective reduction is a doxorubicin semi-synthetic analogue disclosed in our US-A-4438105 (Mar. 20, 1984).

More particularly the present invention relates to a biosynthetic process by which a mutant of the species Streptomyces peucetius, designated strain M 87 F.I. and deposited at the Deutsche Sammlung von Mikroorganismen where it is registered under the accession number DSM 2444, is characterised by its ability to stereoselectively reduce the 13-ketone functional group of 4'-deoxy-4'-iododoxorubican (I). Compound FCE 24883 (II) which results accumulates in the fermentation broths. The FCE 24883 (II) can be recovered from fermentation broths and crude solutions of it concentrated and purified.

The invention therefore also provides a process for the preparation of 4'-deoxy-13(S)-dihydro-4'-iododoxorubicin of formula (II) or a pharmaceutically acceptable salt thereof, which process comprises culturing Streptomyces peucetius strain M 87 F.I. (DSM 2444) in the presence of 4'-deoxy-4'-iododoxorubicin and recovering the resultant 4'-deoxy-13(S)-dihydro-4'-iododoxorubicin as such or in the form of a pharmaceutically acceptable salt.

The invention includes within its scope the new antitumor anthracycline FCE 24883 (II) in the pure form as the hydrochloride.

The invention also provides a pharmaceutical composition comprising compound (II) or a pharmaceutically acceptable salt thereof in admixture with a pharmaceutically acceptable diluent or carrier.

DETAILED DESCRIPTION OF THE INVENTION; THE MICROORGANISM

Streptomyces peucetius subsp. aureus ATCC 31428 has been mutated, using nitrosoguanidine, to give a laboratory microorganism designated Streptomyces peucetius strain M 87 F.I. which selectively transforms compound (I) into compound (II). S. peucetius strain M 87 F.I. has been given the accession number DSM 2444 by Deutsche Sammlung von Mikroorganism, West Germany, where it has been deposited in the permanent collection.

The morphology of the mutant strain M 87 F.I. is indistinguishable from that of the parent S. peucetius ATCC 31428, whereas both cultures are clearly distinguishable in their cultural and biochemical characters. In fact mutant strain M 87 F.I. does not produce on agar media the straw yellow to lemon yellow soluble pigment which characterises its parent S. peucetius ATCC 31428.

Moreover mutant strain M 87 F.I. can selectively transform compound (I) into compound (II) whereas the parent S. peucetius ATCC 31428 is not selective in this respect. This property of mutant M 87 F.I. makes it highly useful, as herein disclosed.

The Transformation Process

The stereoselective biotransformation of the present invention can be effected in a growing culture of S. peucetius strain M 87 F.I. by adding compound I as substrate to the culture during the incubation period.

Compound I, as the hydrochloride, can be added after solubilization in sterile distilled water. The preferred, but not limiting, range of concentration of compound I in the culture is about 50–200 micrograms per liter. The culture is grown in a nutrient medium containing a carbon sources, for example, an assimilable carbohydrate and a nitrogen source, for example an assimilable nitrogen compound or proteinaceous material. Preferred carbon sources include glucose, sucrose, glycerol, starch, corn starch, dextrin, molasses and the like. Preferred nitrogen sources include corn steep liquor, yeast extract, brewer's dry yeast, soy bean meal, cotton seed meal, corn meal, casein, fish meal, distiller's solids, animal peptone, meat extract, ammonium salts and the like. Combination of these carbon and nitrogen sources can be used advantageously. Trace metals, for example, zinc, magnesium, manganese, cobalt, iron and the like, need not necessarily be added to the fermentation media, since tap water and unpurified ingredients are used as components of the medium prior to sterilization.

The biotransformation process can range from about 72 hours to 8 days. The incubation temperature during the biotransformation process can range from about 25° C. to about 37° C., with 29° C. being preferred. The content of the transformation vessels are aerated by shaking at about 250 r.p.m. or by agitating with sterilized air, to facilitate growth of the microorganism, and this enhance the effectiveness of the transformation process.

Analytical Methods

The progress of the microbial transformation reaction is monitored by withdrawing samples of fermentations at various time intervals, and extracting at pH 8.0 with a 9:1 dichloromethane:methanol mixture. When a sample of the organic extract is subjected to thin layer chromatography (TLC), using a eluent a mixture of chloroform:methanol:acetic acid:water 80:20:7:3 (by volume), compound FCE 24883 (II) is found to occur at Rf medium value of 0.50, while 4'-deoxy-4'-iododoxorubicin (I) is found at Rf 0.60. A quantitative estimation of the two anthracyclines can be performed after TLC using the above mentioned eluting systems, by scraping off and eluting with methanol the corresponding red coloured zones and finally spectrophotometric determination at 496 nm.

Isolation Procedure

The whole fermentation broths, in which compound I has been subjected to conversion into FCE 24883 (II), are filtered with the aid of diatomaceous earth. The red mycelial cake is extracted with a water miscible organic solvent, such as methanol and other lower alcohols, dioxane, acetonitrile, acetone, preferentially acetone is employed. The mycelial extracts are collected, concentrated under reduced pressure and combined with the filtered fermentation liquors, adjusted at pH 8.0 then extracted with a water-immiscible organic solvent such as n-butanol, chloroform, dichloromethane, or preferentially a dichloromethane:methanol 9:1 mixture. The organic extracts contain FCE 24883 (II) along with compound I and some minor degradadation products.

Purification Procedure

The organic extract is concentrated under reduced pressure to dryness and the residue, dissolved in dichloromethane, is chromatographed on a column of silica gel, buffered at pH 7, with a gradient of dichloromethane:methanol:water mixture. Compound I is eluted first with a 95:5:0.25 mixture, followed by FCE 24883 (II) with a 90:10:0.5 mixture. From the pooled fractions, after washing with water, concentration to a small volume in the presence of n-propanol, addition of an equivalent of hydrochloric acid and of an excess of n-hexane, a precipitate of pure FCE 24883 (II), as the hydrochloride is obtained.

Chemical and Physical Properties

FCE 24883 (II) as free base is soluble in polar organic solvents and aqueous alcohols, while its hydrochloride is soluble in water and lower alcohols but slighty soluble in organic solvents. The hydrochloride of FCE 24883 has the following physicochemical properties:

melting point: 200° C. (dec.).

specific rotation: $[\alpha]_D^{\leq \circ} + 188°$ (c 0.05, $CH_3OH$).

U.V. and VIS absorption spectrum: $\lambda_{max}^{H2O}$ 232, 254, 290, and 480 nm ($E_{1cm}^{1\%}$ = 492, 370, 127, 163).

I.R. Spectrum (KBr): peaks at the following frequencies: 3400, 2970, 2920, 1610, 1580, 1472, 1440, 1410, 1380, 1355, 1320, 1280, 1235, 1210, 1110, 1080, 1060, 1030, 1010, 985, 965, 940, 920, 900, 890, 870, 860 830, 810, 785, 755, 730, 710, 540, 480, 450 and 415 $cm^{-1}$.

1H—NMR Spectrum (DMSOd$_6$, 200 MHz, 22° C.): 14.03 (bs, 2H, OH—6, OH—11), 7.6-7.9 (m, 3H, H—1, H—2, H—3), 5.26 (m, 1H, H—1'), 4.96 (d, J=5.2 Hz, 1H, OH—13), 4.92 (m, 1H, H—7), 4.55 (m, 1H, H—4'), 4.51 (t, J=6.7 Hz, 1H, OH—14), 4.20 (s, 1H, OH—9), 3.97 (s, 3H, 4—OCH$_3$), 3.76 (ddd, J=3.5, 6.7, 11.0 Hz, 1H, CH(H)—OH), 3.60 (dq, J=1.0, 6.0 Hz, H—5'), 3.48 (ddd, J=7.2, 6.7, 11.0 Hz, 1H, CH(H)—OH), 3.37 (ddd, J=5.2, 3.5, 7.2 Hz, 1H, H—13), 3.02 (m, 1H, H—3'), 2.81 (m, 2H, CH$_2$—10), 2.15 (dd, J=2.0, 15.3 Hz, 1H, H—8e), 1.97 (dd, J=6.0, 15.3 Hz, 1H, H—8ax), 1.7-1.9 (m, 2H, CH$_2$—2') and 1.14 δ(d, J=6.0 Hz, 3H, CH$_3$—5')

Molecular formula: $C_{27}H_{30}NIO_{10} \cdot HCl$— m/z in FD equivalent to the free base: 656|MH|+; 655|M|+; and 416(M+) corresponding to the aglycone.

A selective high pressure liquid chromathography (HPLC) method* allows to separate (two peaks with retention times of 18.8 and 19.3 minutes) the two C—13 stereoisomeric alcohols, present in a sample of synthetic 4'-deoxy-13-dihydro-4'-iododoxorubicin, prepared by NaBH$_4$ reduction of I.

Using the same HPLC method, FCE 24883 (II) appears as a single peak with a retention time of 19.3 minutes corresponding to that of the slower moving constituent of the synthetic 13-dihydroderivative.

*HPLC method

Column: two RP Spherisorb S30DS2 (C18 3μ, Phase Separation U.K.) 150×4.5 mm connected in series.

Temperature: 45° C.

Mobile phase A: 0.05M aqueous of $KH_2PO_4$, made to pH 3.0 with 1M $H_3PO_4/CH_3OH = 80/20$ (by vol.)

Mobile phase B: $CH_3OH$

Elution: isocratic for 30 minutes (42% A + 58% B)

Flow rate: 0.6 ml/min.

Detection: 254 nm.

Structure Elucidation

Acid hydrolysis of II (0.2N aqueous HCl, 80° C., 30 minutes) gives a red precipitate of the corresponding aglycone (III), while the sugar constituent, namely 3-amino-2,3,4,6-tetradeoxy-4-iodo-L-lyxohexohexose, (IV), present in the aqueous phase, has been identified after comparison with comparison with an authentic sample obtained upon acid hydrolysis compound I.

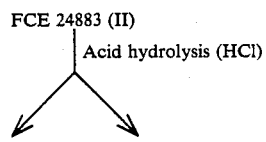

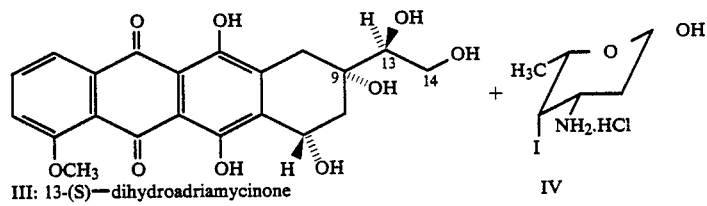

III: 13-(S)—dihydroadriamycinone

IV

The absolute (S)-configuration at C—13 of III has been determined by direct comparison (1H-NMR and mass spectra, TLC) of its 9,13-O-isopropylidene-14-O-t-butyldiphenylsilyl derivative with the corresponding derivative of an authentic samples of 13—(S)-dihydroadriamycinone, obtained as described by S. Penco et al. in Gazzetta Chimica Italiana, 115, 195, 1985.

Biological Activity

The cytotoxic activity of FCE 24883 (II) was tested "in vitro" on HeLa and P 388 cells colony formation in comparison with compound I and doxorubicin. As reported in Table I, compound II resulted as potent as 4'-deoxy-4'-iododoxorubicin (I) and doxorubicin.

The "in vivo" antitumor activity, FCE 24883 (II) was tested against disseminated Gross leukemia. C3H mice were injected intravenously with $2.10^6$ cell/mouse and treated with compounds under study 24 hours after the tumor injection.

Table II shows the results of two experiments. At the optimal dose, FCE 24883 (II), was found more potent than doxorubicin and as potent as 4'-deoxy-4'-iododoxorubicin (I) with a minor toxicity displayed at the active doses. The antitumor activity of compound II, evaluated as median survival time of treated over control mice, can be compared with those of I and doxorubicin.

TABLE 1

In vitro activity of 13-[S]-diidro-4'-Iodo-Doxorubicin (II, FCE 24883) in comparison with 4'-deoxy-4'-Iodo-Doxorubicin (I, FCE 21954) and Doxorubicin (Dx).

| Compound | ID$_{50}$ (ng/ml)[a] | |
| --- | --- | --- |
| | HeLa[b] | P388[c] |
| DX | 10.8 | 8 |
| FCE 21954 (I) | 10.4 | 2.1 |
| FCE 24883 (II) | 8 | 3.5 |

[a]Dose giving 50% reduction of cell number in comparison with untreated controls.
[b]Human cervix epithelioid carcinoma cells.
[c]P388 leukemia cells.

TABLE 2

Activity of 13-[S]-diidro-4'-Iodo-Doxorubicin (II, FCE 24883) in comparison with 4'-deoxy-4'-Iodo-Doxorubicin (I, FCE 21954) and Doxorubicin (DX) against disseminated Gross leukemia.

| Compound | Dose[a] (mg/Kg) | T/C %[b] | Toxic deaths[c] |
| --- | --- | --- | --- |
| DX | 10 | 200 (200, 200) | 0/20 |
| | 13 | 225 (230, 220) | 0/20 |
| | 16.9 | 250 (260, 240) | 2/20 |
| FCE 21954 (I) | 4 | 240 (240, 240) | 0/20 |
| | 5.2 | 260 (260, 260) | 4/20 |
| | 6.8 | 145 (160, 130) | 19/20 |
| FCE 24883 (II) | 4 | 180 (180) | 0/10 |
| | 5.2 | 220 (220, 220) | 0/20 |
| | 6.8 | 220 (220, 220) | 0/20 |
| | 8.8 | 140 (140) | 5/9 |

[a]C3H mice were injected i.v. with $2 \times 10^6$ leukemia cells and treated i.v. with the compounds the day after the tumor injection.
[b](Median survival time of treated mice/median survival time of controls) $\times$ 100
[c]Evaluated on the basis of autopsy findings on dead mice.

DESCRIPTION OF THE PREFERRED EMBODIMENTS

The following non-limitative examples are given in order to describe in more detail the processes and the product of the subject invention.

EXAMPLE 1

A culture of *Streptomyces peucetius*, strain M 87 F.I. (DSM 2444) has been grown for 14 days at 28° C. on agar slants of the following maintenance medium (medium SA): glucose, 3%; brewer's dry yeast, 1.2%; NaCl, 0.1%; KH$_2$PO$_4$, 0.05%; CaCO$_3$, 0.1%; MgSO$_4$, 0.005%; FeSO$_4$.7H$_2$O, 0.0005%; ZnSO$_4$.7H$_2$O, 0.0005%; CuSO$_4$.5H$_2$O, 0.0005%; agar, 2%; tap water up to 100 ml; pH 6.7; sterilization is carried out by heating in an autoclave at 115° C. for 20 minutes.

The spores of the so grown culture are collected and suspended in 3 ml of sterile distilled water; this suspension is inoculated in 300 ml Erlenmeyer flasks containing 60 ml of the following liquid growth medium: brewer's dry yeast, 0.3%; peptone, 0.5%; Ca(NO$_3$)$_2$.4H$_2$O, 0.05%; tap water up to 100 ml. Sterilization by heating in autoclave at 120° C. for 20 minutes. The pH of this medium after sterilization is between 6.8 and 7.0. The inoculated flasks are shaken for 2 days at a temperature of 28° C. on a rotary shaker running at 250 r.p.m. and describing a circle of 7 cm in diametr. 1.5 ml of the culture grown as described above are inoculated in 300 ml Erlenmeyer flasks containing 50 ml of the following biotransformation medium: yeast extract, 1.5%; KH$_2$PO$_4$, 0.25%; glucose, 1.5%; tap water up to 100 ml, pH 6.9; sterilization by heating in autoclave at 115° C. for 20 minutes. The glucose solution is sterilized separately and added to each sterilized flask at the proper concentration.

The flasks are then incubated at 28° C. under the conditions described for the seed phase, for 24 hours. At this time 1.0 ml of a solution of compound I in sterile distilled water at a concentration of 5 mg/ml are added to each flasks. The shaken flasks are incubated for 2 days more obtaining a 70% conversion of compound I into compound II.

EXAMPLE 2

A culture of *S. peucetius* strain M 87 F.I. is grown on solid medium as described in example 1. The spores of three slants are pooled and collected in 10 ml of sterile distilled water; the suspension so obtained is inoculated in a 2 l baffled round-bottomed flask containing 500 ml of the seed medium described for example 1. The flask is incubated for 48 hours on a rotary shaker running at 120 r.p.m. and describing a circle of 7 cm in diameter at a temperature of 28° C. The whole seed is inoculed in a 10 l stainless-steel fermenter containing 7.5 l of the biotransformation medium described in example 1 and sterilized by vapour at 120° C. for 30 minutes, the glucose solution being sterilized separately and added at the proper concentration of the sterilized fermenter. The culture is allowed to grow at 28° C. under stirring at 230 r.p.m. and aerated with an air flow of 0.7 liter/liter of the medium/minute. After 48 hours the substrate compound is added at the concentration described for example 1, and the culture incubated for 3 more days obtaining a 60% conversion of compound I into compound II.

EXAMPLE 3

The whole beer (5 l) from a fermentation obtained according to example 2, was filtered using 2% diatomaceous earth as filter aid. The wet filter cake was extracted with acetone (3 l). After filtration two additional extractions with acetone were effected to ensure a complete recovery of the red pigments. The combined acetone extracts were concentrated under reduced pressure and the concentrate (1 l) was combined with the filtered broth and exhaustively extracted at pH 8 with a dichloromethane:methanol 9:1 mixture. The organic extract, containing compounds I and II with some degradation products, was concentrated under reduced pressure to dryness. The residue, dissolved in dichloromethane, was chromatographed on a column of silica gel, buffered at pH 7, (M/15 phosphate buffer) with a gradient of dichloromethane:methanol:water mixture. After some degradation products compound I was eluted with a 95:5:0.25 mixture followed by FCE 24883 (II) with a 90:10:0.5 mixture.

From the pooled fractions, after washing with water, concentration to a small volume in the presence of n-propanol, addition of an equivalent of hydrochloric acid and of an excess of n-hexane pure FCE 24883 (II, 0.30 g, 60%), as the hydrochloride (m.p. 200° C., dec.) was obtained. Following the same procedure, untransformed compound I (0.13 g, 26%), as the hydrochloride was also recovered.

EXAMPLE 4

A sample of FCE 24833 (I) (200 mg) was dissolved in 0.2N aqueous hydrochloric acid (50 ml) and heated for 30' at 100° C. A crystalline red precipitate (0.12 g) of aglycone (III) was collected by filtration, washed with water and dried. Mass spectrum: m/e 416 (M+). The aglycone (III) was identified as 13—(S)-dihydroadriamycinone by comparison with an authentic sample.

We claim:

1. 4'-Deoxy-13(S)-dihydro-4'-iododoxorubicin having the formula (II)

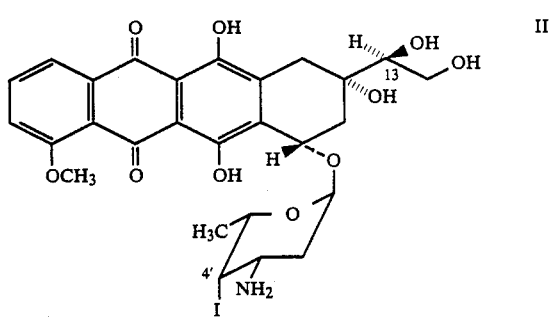

and pharmaceutically acceptable salts thereof.

2. The compound according to claim 1 wherein the salt is the hydrochloride.

* * * * *